United States Patent [19]

LaMattina et al.

[11] 4,443,621

[45] Apr. 17, 1984

[54] P-NITROPHENYL 3-BROMO-2,2-DIETHOXY-PROPIONATE AND SYNTHETIC UTILITY THEREFOR

[75] Inventors: John L. LaMattina, Ledyard; Paul D. Weeks, Gales Ferry, both of Conn.

[73] Assignee: Pfizer Inc., New York, N.Y.

[21] Appl. No.: 474,958

[22] Filed: Mar. 14, 1983

[51] Int. Cl.³ .................... C07C 79/12; C07D 309/40
[52] U.S. Cl. ..................................... 560/142; 549/418
[58] Field of Search ........................................ 560/142

[56] References Cited

U.S. PATENT DOCUMENTS

| | | | |
|---|---|---|---|
| 3,130,204 | 4/1964 | Tate et al. | 549/418 |
| 3,365,469 | 1/1968 | Tate et al. | 549/418 |
| 3,468,915 | 9/1969 | Tate | 549/418 |
| 3,644,635 | 2/1972 | Tate et al. | 424/283 |
| 4,082,717 | 4/1978 | Brennan et al. | 549/418 |
| 4,282,151 | 8/1981 | Batz et al. | 560/142 |

*Primary Examiner*—Glennon H. Hollrah
*Assistant Examiner*—Patricia M. Scott
*Attorney, Agent, or Firm*—Charles J. Knuth; Albert E. Frost; Robert K. Blackwood

[57] ABSTRACT p-Nitrophenyl 3-bromo-2,2-diethoxypropionate, useful in the synthesis of highly functionalized small molecules and heterocycles, including pyromeconic acid and 6-methylpyromeconic acid.

1 Claim, No Drawings

METHOD FOR MAKING CARBAMATES

This is a continuation, of application Ser. No. 263,880 filed May 15, 1981, now abandoned which in turn is a continuation of application Ser. No. 83,514 filed Oct. 10, 1979, now abandoned.

The present invention relates to the manufacture of alkyl carbamates from urea and aliphatic alcohols. In accordance with the invention, a vacuum is applied, and preferably a magnesium catalyst is used. The vacuum significantly accelerates the reaction, thereby reducing the cost of manufacture.

BACKGROUND OF THE INVENTION

Alkyl carbamates are useful as intermediates for making textile cross-linking resins and as intermediates in the manufacture of pharmaceuticals. A number of procedures for manufacturing them have been described, e.g., in U.S. Pat. No. 3,574,711. In particular, it is known to manufacture them by reaction of urea with an aliphatic alcohol according to the reaction:

$$R-OH + NH_2CONH_2 \rightarrow ROCONH_2 + NH_3$$

U.S. Pat. No. 2,837,571 describes the use or cupric salts as catalysts for this reaction. U.S. Pat. No. 3,574,711 discloses the possibility of conducting the reaction without a catalyst and also the use of zinc catalysts such as zinc acetate, zinc formate, zinc carbonate, or zinc oxide. These prior patents disclose heating the reactants at elevated temperatures such as 110° to 200° C. at atmospheric pressure. Liberated ammonia may be collected, e.g., in a dry ice trap. Following completion of the reaction, the products are recovered by distillation, e.g., under vacuum.

SUMMARY OF THE INVENTION

In accordance with the present invention, it has been found that the application of vacuum to the reaction accelerates the reaction when carried out either without catalyst or using catalyst described previously. Furthermore, it has been found that the reaction can be accelerated by magnesium compounds. The use of vacuum when magnesium compounds are employed, has produced an especially useful effect.

DETAILED DESCRIPTION

The invention is applicable to a wide variety of alcohols i.e., alcohols having the formula $R(OH)_n$ wherein R is an organic group and n is a whole number. R may be an aliphatic group, saturated or unsaturated, or it may be aromatic or arylaliphatic. However, the invention is particularly applicable to higher alcohols which are not excessively volatile under the temperature and pressure conditions applied in the reaction. For example, using a vacuum of 28 inches, isopropyl alcohol was found to be too volatile. The invention is applicable to alcohols containing one, or more than one, hydroxyl group. The invention is particularly useful with diethylene glycol, whose carbamate is particularly suited for the manufacturing of textile resins.

The vacuum applied should be sufficient to accelerate the rate of reaction. In this specification, vacuum is given in inches of mercury.) A vacuum of 10 inches or more may be used. It has been found, however, that at 10 inches, the condenser used to trap entrained alcohol became clogged with a solid, which may be ammonium carbamate. This problem was not encountered at higher vacuums, such as 20-28 inches. Especially useful results may be achieved at 28 inches, although it is believed that still higher vacuums may be beneficial and economically useful.

The vacuum selected must be related to the vapor pressure of the alcohol which may be affected by dissolved urea and/or carbamate. If the vapor pressure is too high, the alcohol may be entrained with escaping ammonia to an excessive degree. To some extent this problem may be controlled by passing the effluent from the reaction through a condenser which traps alcohol, and the trapped alcohol may be returned to the reaction vessel. However, too high a vacuum may, in the case of some alcohols, cause too much entrainment.

One of the advantages of the present invention is that it may be carried out at molar ratios of urea to alcohol that are very nearly 1:1. Using such ratios, a relatively uncontaminated product may be obtained directly, with little or no need for purification. The preferred ratio is 1.1 moles urea for each mole of alcohol. However, it will be appreciated that other ratios may be used, including excess of either alcohol of urea. The temperature of the reaction has not been found to be critical. Initially, a temperature of 150° C. was thought to be preferable, but a temperature of 160° C. is now preferred. Still higher temperatures may be used, e.g., up to 200° C. However, the increased rate of reaction achieved must be evaluated against the increased energy cost of such high temperatures. Conversely, lower temperatures may be used, e.g., down to 130° C., although slower reactions result from lower temperatures.

The process under vacuum may be conducted with no catalyst. However, the reaction speed is increased with catalyst. Conversely, the proportion of the starting materials which react in a selected cycle time is increased with catalysts.

A preferred catalyst is a magnesium compound, especially magnesium oxide. Magnesium oxide is supplied in various grades, according to reactivity, which in turn depends on degree of calcination. The grades are characterized by the speed with which they neutralize acid. The grades are understood to differ in their degree of calcination, hardness and granularity. For purposes of the present invention, high reactivity types are preferred. Particularly useful is Magox 98HR, supplied by Basic Chemicals, a division of Basic Incorporated, Cleveland, Ohio. It is characterized by the following properties:

CHEMICAL COMPOSITION

|  | Typical | Minimum | Maximum |
|---|---|---|---|
| Analysis |  |  |  |
| Loss on Ignition at 1370° C. | 5.0% |  | 6.0% |
| Iodine No., meq/100 gms | 45 | 35 |  |
| Chloride (as Cl) | 0.2% |  | 0.4% |
| Sulfate (as $SO_3$) | 0.55% |  | 0.7% |
| Loss Proc Basis |  |  |  |
| MgO | 97.1% | 97.0% |  |
| CaO | 1.8% |  | 2.0% |
| $SiO_2$ | 0.6% |  | 0.9% |
| $R_2O_3$ | 0.5% |  |  |
| PHYSICAL PROPERTIES |  |  |  |
| Sizing | 99.0%–200 mesh* | | |
| Bulk Density, Loose (approximate) | 25 lbs./ft. 3 | | |

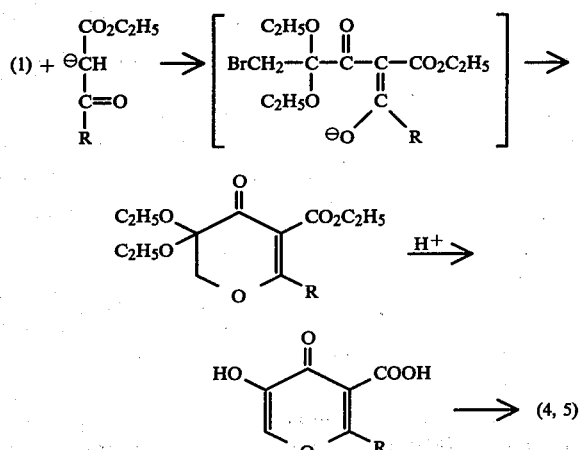

(6) R=CH₃
(7) R=H
(8) R=CH₃
(9) R=H as exemplified below.

Heterocyclic molecules are also derived from the above polyfunctional small molecules, which behave similarly. For example, 5-bromo-4,4-diethoxy-3-oxovaleronitrile is reacted with hydrazine, forming (via hydrazone formation, cyclization and ethanol elimination) 3-cyanomethyl-4-ethoxypyrazole; and acetimido 3-bromo-2,2-diethoxypropionate is cyclized on warming to produce 3-methyl-5-(2-bromo-1,1-diethoxyethyl)-1,2,5-oxadiazole. The latter is deketalized by warming in 95% formic acid to produce the corresponding 3-methyl-5-(2-bromoacetyl)-1,2,5-oxadiazole.

The present invention is illustrated by the following Examples. However, it should be understood that the invention is not limited to the specific details of these Examples.

EXAMPLE 1

3-Bromo-2,2-diethoxypropionate Acid alpha-Bromopyruvic acid (100 g, 0.60 mole), 240 mL triethyl orthoformate and H₂SO₄ (4 mL) were combined and the resulting solution stirred 24 hours, then diluted with 1.2 L CH₂Cl₂. The organic phase was separated, washed 2×100 mL H₂O and then 1×100 mL saturated NaCl, dried over Na₂SO₄, evaporated and dried in vacuo 4 hours to yield title product as a white solid, 144 g (99%); mp 80°–85° C. This product was of sufficient purity for direct use in the next step. A sample recrystallized from cyclohexane gave mp 91°–92° C.

EXAMPLE 2 p-Nitrophenyl 3-Bromo-2,2-diethoxypropionate (NPBDP 1)

Title product of the preceding Example (144 g, 0.60 mole), p-nitrophenyl trifluoroacetate (141 g; 0.60 mole), and pyridine (405 mL) were stirred under N₂ for 24 hours, then poured into 2 L H₂O and extracted 4×500 mL ether. The extracts were combined, washed 5×175 mL 5% NaOH, dried over Na₂SO₄, and evaporated to an oil which crystallized on scratching. Recrystallization from hexane gave purified title product as a stable, white crystalline solid; 169 g (77%), mp 75°–76° C.

EXAMPLE 3

Ethyl 2,3-Dihydro-3,3-diethoxy-6-methyl-4-pyrone-5-carboxylate (6)

Under N₂, NaH (1.06 g, 44 mmole) was stirred in 100 mL dry tetrahydrofuran (THF). A solution of ethyl acetoacetate (5.47 g, 42 mmole) in 20 mL of dry THF was added dropwise over 15 minutes, followed by NPBDP (7.24 g, 20 mmole) in 80 mL dry THF over 5 minutes. The resulting mixture was refluxed for 4 hours, cooled, poured into 400 mL ice water, adjusted to pH 7 with 1 N HBr, and extracted 3×80 mL CHCl₃. The extracts were combined, dried over Na₂SO₄ and evaporated to an oil. The oil was chromatographed on 260 g silica gel, using isopropyl ether as eluant. Following elution of less polar ethyl acetoacetate and p-nitrophenol, title product eluted as an oil which distilled in vacuo to yield purified title product; 3.46 g (63%); bp 110°–115° C./0.2 mm.

Anal. Calcd. for C₁₃H₂₀O₆: C, 57.34; H, 7.40; Found: C, 57.12; H, 7.28.

Substituting an equivalent amount of ethyl formylacetate for ethyl acetoacetate yields ethyl 2,3-dihydro-3,3-diethoxy-4-pyrone-5-carboxylate (7).

EXAMPLE 4

2-Methyl-5-hydroxy-4-pyrone-3-carboxylic Acid (8)

Under nitrogen, a solution of title product of the preceding Example (3.46 g) is heated in 95% formic acid at 85° C. for 1 hour. The mixture is cooled and evaporated in vacuo to yield present title product.

In like manner, compound (7) of the preceding Example is converted to 5-hydroxy-4-pyrone-3-carboxylic acid (9).

EXAMPLE 5

6-Methylpyromeconic Acid (4)

Title product of the preceding Example (3.0 g, 0.012 mole) is stirred with 12 mL of dimethyl phthalate and heated to 220°–240° C. until evolution of carbon dioxide is complete (about 15 minutes). The mixture is cooled to about 80° C. and fractionally distilled in vacuum at 1–10 mm. Title product is found in fractions distilling below the boiling point of dimethyl phthalate, which is 148° C./10 mm, 132°/5 mm and 100° C./1 mm.

In the same manner, compound (9) of the preceding Example is converted to pyromeconic acid.

We claim:
1. p-Nitrophenyl 3-bromo-2,2-diethoxypropionate.

* * * * *

-continued

| Time | Temp. | Rate | Residual Urea | Ext. of React |
|---|---|---|---|---|
| 13:40 | 150 | 6.2 | 1.129 | 0.872 |
| 14:10 | 151 | 4.3 | 0.971 | 0.890 |

EXAMPLE II

Four experiments were conducted in the same equipment as Example I, to evaluate the effect of various degrees of vacuu. In each case, the reactants were 848 grams diethylene glycol, 528 grams urea and 1.5 grams magnesium oxide. In each case, heat was applied at the same rate until the temperature reached 150° C. Then the temperature was maintained at about 150° C. for 3 hours. After 3 hours, the amount of urea was measured. It was found that the amount of urea decreased progressively as the pressure in the flask was reduced. (In two cases, the flask was then heated to 160° and reacted for two additional hours.) The vacuums used were:

A. 20 inches
B. 25 inches
C. 26 inches
D. 27 inches

The heating schedules and residual urea measurements were as follows:

| Time | Temp. | |
|---|---|---|
| EXPERIMENT A | | |
| 8:20 | 25° C. | |
| 9:12 | 110° C. | |
| 9:50 | 140° C. | |
| 10:25 | 146° C. | |
| 10:47 | 149° C. | |
| 10:55 | 150° C. | |
| 11:00 | 151° C. | |
| 11:25 | 151° C. | |
| 11:47 | 152° C. | |
| 11:55 | 152° C. | |
| 12:20 | 148° C. | |
| 12:35 | 147° C. | |
| 12:50 | 150° C. | |
| 1:00 | 151° C. | |
| 1:14 | 152° C. | |
| 1:55 | 151° C. | 10.8% urea |
| EXPERIMENT B | | |
| 8:14 | 25° C. | |
| 8:36 | 60° C. | |
| 8:47 | 76° C. | |
| 9:07 | 111° C. | |
| 9:30 | 133° C. | |
| 9:52 | 140+° C. | |
| 10:15 | 144+° C. | |
| 10:41 | 147° C. | |
| 10:56 | 150° C. | |
| 11:04 | 149+° C. | |
| 11:10 | 149° C. | |
| 11:36 | 151° C. | |
| 11:48 | 152° C. | |
| 12:08 | 149° C. | |
| 12:20 | 150° C. | |
| 12:32 | 151° C. | |
| 12:55 | 150° C. | |
| 1:05 | 149° C.+ | |
| 1:45 | 151° C. | 7.0% urea |
| 2:10 | 148° C. | |
| 2:30 | 150° C.+ | |
| 2:56 | 148° C. | 6.28% urea |
| 3:47 | 150° C. | |
| EXPERIMENT C | | |
| 7:55 | 25° C. | |
| 8:17 | 56° C. | |
| 8:43 | 99° C. | |
| 8:54 | 115° C. | |
| 9:05 | 125° C. | |
| 9:37 | 140° C. | |
| 10:36 | 147° C. | |
| 10:49 | 150° C. | |
| 11:15 | 151° C. | |
| 11:19 | 151°+ C. | |
| 11:30 | 151° C. | |
| 11:48 | 151°+ C. | |
| 12:15 | 150° C. | |
| 12:30 | 149°+ C. | |
| 12:43 | 150°+ C. | |
| 12:49 | 151° C. | 5.92% urea |
| 1:40 | 150° C. | |
| 1:49 | 150° C. | 5.32% urea |
| 2:20 | 160° C. | |
| 2:27 | 161° C. | |
| 2:49 | 160° C. | 4.31% urea |
| 3:49 | 160°+ C. | |
| EXPERIMENT D | | |
| 8:07 | 25° C. | |
| 8:25 | 50° C. | |
| 8:40 | 75° C. | |
| 8:54 | 99° C. | |
| 9:15 | 125° C. | |
| 9:50 | 140° C. | |
| 10:45 | 147° C. | |
| 11:10 | 150° C. | |
| 11:23 | 149° C.+ | |
| 11:36 | 150° C. | |
| 11:42 | 151° C. | |
| 11:52 | 151° C.+ | |
| 12:00 | 152° C. | |
| 12:10 | 150° C. | |
| 12:15 | 149° C.+ | |
| 12:24 | 150° C. | |
| 12:28 | 150° C.+ | |
| 12:35 | 151° C.+ | |
| 12:40 | 152° C. | |
| 12:52 | 149° C.+ | |
| 1:00 | 149° C. | |
| 1:10 | 150° C. | 4.98% urea |
| 1:23 | 151° C. | |
| 2:10 | 150° C. | 4.28% urea |
| 2:22 | 150° C. | |
| 2:50 | 160° C. | |
| 3:10 | 160° C. | 3.93% urea |

EXAMPLE III

To compare the effect of various catalysts, experiments were conducted in the equipment described in Example I at 28 inches vacuum. In each, 848 grams diethylene glycol (8 moles) were reacted with 528 grams urea (8.8 moles). The catalysts were as follows:

A. 1.5 grams magnesium oxide
B. 1.5 grams calcium oxide
C. 1.5 grams zinc oxide

The results demonstrated the superior effectiveness of magnesium oxide.

| Ammonia | Time | Temp. |
|---|---|---|
| EXPERIMENT A | | |
| | 8:10 | 25° C. |
| | 8:25 | 51° C. |
| | 8:35 | 69° C. |
| | 8:45 | 84° C. |
| 0.0 g NH$_3$/min | 8:54 | 99° C. |
| 0.271 g NH$_3$/min | 9:16 | 125° C. |
| 0.496 g NH$_3$/min | 9:27 | 132° C. |
| 0.733 g NH$_3$/min | 9:42 | 137° C. |
| 0.831 g NH$_3$/min | 10:25 | 142° C. |
| 0.792 g NH$_3$/min | 10:45 | 143° C.+ |
| 0.743 g NH$_3$/min | 11:15 | 147° C. |
| 0.265 g NH$_3$/min | 1:00 | 151° C.+ |
| 0.166 g NH$_3$/min | 1:30 | 151° C. |

-continued

| Ammonia | Time | Temp. |
|---|---|---|
| 0.121 g NH₃/min | 2:00 | 150° C. |
| 0.080 g NH₃/min | 2:30 | 150° C. |
| 0.071 g NH₃/min | 3:00 | 150° C. |
| 0.068 g NH₃/min | 3:30 | 151° C. |

EXPERIMENT B

| Ammonia | Time | Temp. |
|---|---|---|
|  | 8:06 | 22° C. |
|  | 8:25 | 56° C. |
|  | 8:35 | — |
|  | 8:40 | 84° C. |
| 0.048 g/min | 8:50 | 99° C. |
| 0.199 g/min | 9:15 | 122° C. |
| 0.445 g/min | 9:30 | 135° C. |
| 0.771 g/min | 10:00 | 142° C. |
| 0.758 g/min | 10:30 | 145° C. |
| 0.703 g/min | 11:00 | 148° C. |
|  | 11:30 | 150° C. |
| 0.294 g/min | 12:30 | 150° C. |
| 0.172 g/min | 1:00 | 149° C. |
| 0.126 g/min | 1:30 | 150° C. |
| 0.097 g/min | 2:00 | 150° C.+ |
| 0.027 g/min | 2:30 | 150° C. |
| 0.046 g/min | 3:00 | 150° C. |
|  | 3:30 - OFF | |

EXPERIMENT C

| Ammonia | Time | Temp. |
|---|---|---|
|  | 7:40 | 25° C. |
|  | 8:00 | 65° C. |
|  | 8:05 | 74° C. |
|  | 8:12 | 86° C. |
| 0.0 g NH₃/min | 8:20 | 99° C. |
| 0.229 g NH₃/min | 8:44 | 125° C. |
| 0.377 g NH₃/min | 8:55 | 132° C. |
| 0.521 g NH₃/min | 9:04 | 137° C. |
| 0.621 g NH₃/min | 9:16 | 140° C. |
| 0.658 g NH₃/min | 9:35 | 142° C. |
| 0.635 g NH₃/min | 9:56 | 144° C. |
| 0.613 g NH₃/min | 10:21 | 146° C. |
| 0.577 g NH₃/min | 10:45 | 148° C. |
| 0.534 g NH₃/min | 11:10 | 150° C. |
| 0.499 g NH₃/min | 11:40 | 151° C. |
| 0.320 g NH₃/min | 12:10 | 151° C. |
| 0.201 g NH₃/min | 12:40 | 150° C. |
| 0.178 g NH₃/min | 1:10 | 151° C. |
| 0.114 g NH₃/min | 1:40 | 150° C. |
| 0.095 g NH₃/min | 2:10 | 151° C. |

EXAMPLE IV

The following experiment illustrates the use of sufficient urea to react with both hydroxl groups of diethylene glycol. The equipment used was the same as Example I, and the vacuum was 28 inches. The reactants were 742 grams diethylene glycol (7 moles) 840 grams urea (14 moles), and 3 grams magnesium oxide. The heating sequence was as follows:

| Time | Temp. |
|---|---|
| 8:07 | 54° C. |
| 8:30 | 77° C. |
| 8:47 | 96° C. |
| 9:08 | 119° C. |
| 9:34 | 132° C. |
| 9:53 | 135° C. |
| 10:10 | 137° C. |
| 10:32 | 138° C. |
| 10:58 | 140° C. |
| 11:17 | 141° C. |
| 11:47 | 145° C. |
| 12:10 | 147° C. |
| 12:32 | 149° C. |
| 12:36 | 150° C. |
| 12:47 | 151° C. |
| 1:03 | 151° C.+ |
| 1:28 | 149° C.+ |
| 1:35 | 150° C. |
| 1:50 | 152° C.+ |

-continued

| Time | Temp. |
|---|---|
| 1:59 | 152° C.+ |
| 2:31 | 151° C. |
| 3:28 | 152° C.+ |
| 3:32 | 152° C. |
| 4:53 | 151° C. |

The product contained 7.3% urea.

EXAMPLE V

In the equipment described in Example I, the following materials were reacted at 28 inches vacuum:

| | |
|---|---|
| Neodol 253 (a hydroxyl-ended polyether derived from 3 moles ethylene oxide and a 12 carbon atom alcohol) | 668 grams (2 moles) |
| Urea | 132 grams (2.2 moles) |
| Magnesium oxide | 2.4 grams |

The heating sequence was as follows:

| Time | Temp. |
|---|---|
| 7:53 | 22° C. |
| 8:04 | 101° C. |
| 8:09 | 120° C. |
| 8:14 | 125° C. |
| 8:24 | 150° C. |
| 8:25 | 150° C.+ |
| 8:34 | 151° C. |
| 8:42 | 150° C. |
| 8:53 | 151° C.+ |
| 8:57 | 152° C. |
| 9:05 | 153° C. |
| 9:12 | 153° C. |
| 9:20 | 150° C. |
| 9:24 | 149° C. |
| 9:35 | 148° C. |
| 9:50 | 150° C. |

EXAMPLE VI

In the equipment described in Example I, the following materials were reacted at 28 inches vacuum:

| | |
|---|---|
| Neodol 253 | 200 grams |
| Diethylene glycol | 600 grams |
| Urea | 414 grams |
| Magnesium oxide | 3 grams |

The heating sequence was as follows:

| Time | Temp. |
|---|---|
| 10:00 | 22° C. |
| 10:25 | 98° C. |
| 10:34 | 123° C. |
| 11:14 | 150° C. |
| 11:19 | 152° C. |
| 11:55 | 153° C. |
| 12:17 | 153° C. |
| 12:42 | 153° C. |
| 1:43 | 152° C. |
| 1:51 | 152° C. |
| 2:14 | 150° C. |

EXAMPLE VII

In the equipment described in Example I, the following materials were reacted at approximately 15 inches of vacuum:

| methyl carbitol | 480 grams |
|---|---|
| urea | 240 grams |
| magnesium oxide | 1.5 grams |

The heating sequence was as follows:

| Time | Temp. |
|---|---|
| 8:00 | 25° C. |
| 8:14 | 68° C. |
| 8:35 | 127° C. |
| 8:50 | 148° C. |
| 9:06 | 148° C. |
| 9:15 | 150° C. |
| 9:30 | 153° C. |
| 9:45 | 148° C. |
| 10:13 | 148° C. |
| 10:23 | 148° C.+ |
| 10:27 | 150° C. |
| 10:37 | 151° C. |
| 10:42 | 152° C. |
| 10:57 | 152° C. |
| 11:00 | 153° C. |
| 11:10 | 152° C.+ |
| 11:35 | 150° C. |

EXAMPLE VIII

In the equipment described in Example I, the following materials were reacted at approximately 28 inches of vacuum:

| butyl carbitol | 525.6 grams |
|---|---|
| urea | 194.4 grams |
| magnesium oxide | 1.5 grams |

The heating sequence was as follows:

| Time | Temp. |
|---|---|
| 8:10 | 25° C. |
| 8:36 | 115° C. |
| 8:42 | 123° C. |
| 8:58 | 150° C. |
| 9:08 | 151° C. |
| 9:29 | 153° C. |
| 9:35 | 154° C. |
| 9:40 | 153° C. |
| 9:47 | 152° C. |
| 9:55 | 150° C. |
| 10:05 | 150° C. |
| 10:13 | 140° C. |
| 10:25 | 136° C. |
| 11:03 | 138° C. |
| 11:25 | 140° C. |

EXAMPLE IX

In the equipment described in Example I, the following materials were reacted at approximately 28 inches of vacuum:

| Dow Corning Q43557 (hydroxy group-containing silicone) | 400 grams |
|---|---|
| urea | 60 grams |
| magnesium oxide | 0.5 grams |

The heating sequence was as follows:

| Time | Temp. |
|---|---|
| 8:12 | 25° C. |
| 8:35 | 120° C. |
| 9:25 | 144° C. |
| 9:45 | 150° C. |
| 9:57 | 153° C. |
| 10:46 | 150° C. |

EXAMPLE X

In the equipment described in Example I, the following materials were reacted at 28 inches vacuum:

| Dow Corning Q4-3667 (hydroxy group containing silicone) | 400 grams |
|---|---|
| urea | 22 grams |
| magnesium oxide | 0.84 grams |

The heating sequence was as follows:

| Time | Temp. |
|---|---|
| 8:11 | 25° C. |
| 8:35 | 120° C. |
| 8:48 | 147° C. |
| 8:50 | 151° C. |
| 8:52 | 155° C. |
| 8:55 | 159° C. |
| 8:57 | 154° C. |
| 9:02 | 146° C. |
| 9:05 | 146° C. |
| 9:10 | 151° C. |
| 9:14 | 154° C. |
| 9:16 | 157° C. |
| 9:25 | 148° C. |
| 9:37 | 146° C. |
| 9:54 | 152° C. |
| 10:26 | 140° C. |
| 11:00 | 152° C. |

EXAMPLE XI

In the equipment described in Example I, the following materials were reacted at 28 inches of vacuum (the vacuum was kept lower at the start of heating, and until foaming ended):

| Sorbitol | 438 grams (2.4 moles) |
|---|---|
| urea | 162 grams (2.7 moles) |
| magnesium oxide | 1.2 grams |

The heating sequence was as follows:

| Time | Temp. |
|---|---|
| 9:25 | 111° C. |
| 9:28 | 118° C. |
| 9:35 | 131° C. |
| 9:38 | 128° C. |
| 9:57 | 142° C. |
| 10:07 | 144° C. |
| 10:11 | 150° C. |
| 10:12 | 151° C. |
| 10:15 | 153° C. |

-continued

| Time | Temp. |
|---|---|
| 10:18 | 153° C. |
| 10:21 | 154° C. |
| 10:39 | 154° C. |
| 10:41 | 155° C. |
| 10:46 | 156° C. |
| 10:55 | 154° C. |
| 11:10 | 146° C. |
| 11:16 | 146° C. |

EXAMPLE XII

In the equipment described in Example I, the following materials were reacted at 28 inches vacuum:

| | |
|---|---|
| Diethylene glygol | 500 grams |
| Dow Corning Q4-3667 | 100 grams |
| Urea | 572 grams |
| Magnesium oxide | 2.3 grams |

The heating sequence was as follows:

| Time | Temp. |
|---|---|
| 8:15 | on |
| 9:00 | 149° |
| 9:05 | 150° |
| 9:08 | 152° |
| 9:20 | 145° |
| 9:30 | 152° |
| 10:00 | 150° |
| 10:30 | 150° |

EXAMPLE XIII

In the equipment described in Example I, the following materials were reacted at 28 inches vacuum:

| | |
|---|---|
| Diethylene glycol | 848 grams |
| Urea | 528 grams |

The experiment was conducted twice, using the following catalysts in respective experiments:
A. magnesium oxide—1.5 grams
B. calcium oxide—1.5 grams
The heating sequences were as follows:

| Time | Temp. |
|---|---|
| EXPERIMENT A | |
| 8:33 | 32° C. |
| 8:52 | 64° C. |
| 9:01 | 77° C. |
| 9:07 | 86° C. |
| 9:13 | 95° C. |
| 9:16 | 100° C. |
| 9:24 | 108° C. |
| 9:30 | 112° C. |
| 9:37 | 119° C. |
| 9:45 | 125° C. |
| 9:55 | 129° C. |
| 10:00 | 131° C. |
| 10:15 | 134° C. |
| 10:30 | 135° C.+ |
| 10:45 | 136° C.+ |
| 11:00 | 137° C.+ |
| 11:15 | 138° C. |
| 11:30 | 139° C. |
| 11:45 | 140° C. |
| 12:00 | 141° C. |
| 12:15 | 142° C. |
| 12:30 | 143° C. |
| 12:45 | 144° C.+ |
| 1:00 | 146° C. |
| 1:26 | 148° C. |
| 1:45 | 150° C. |
| 2:10 | 150° C.+ |
| 2:23 | 151° C. |
| 2:37 | 151° C. |
| 2:45 | 150° C. |
| 3:05 | 148° C. |
| 3:40 | 152° C. |
| EXPERIMENT B | |
| 7:57 | 19° C. |
| 8:14 | 48° C. |
| 8:20 | 60° C. |
| 8:28 | 71° C. |
| 8:43 | 94° C. |
| 8:52 | 105° C. |
| 9:04 | 119° C. |
| 9:15 | 127° C. |
| 9:30 | 134° C. |
| 9:45 | 137° C. |
| 10:00 | 138° C.+ |
| 10:15 | 139° C.+ |
| 10:30 | 140° C.+ |
| 11:00 | 142° C.+ |
| 11:15 | 143° C.+ |
| 11:30 | 144° C.+ |
| 12:15 | 148° C. |
| 12:45 | 150° C. |
| 1:00 | 150° C.+ |
| 1:15 | 150° C.+ |
| 1:30 | 151° C. |
| 1:45 | 150° C. |
| 2:00 | 150° C.+ |
| 2:15 | 150° C.+ |
| 2:30 | 152° C. |
| 3:00 | 148° C. |
| 3:15 | 148° C.+ |
| 3:45 | 150° C. |

In the first experiment, the urea content was reduced to 2.7% at 2:45 whereas in the second experiment, the urea content was 4.17% at 1:45 and 3:17% at 3:00. Therefore magnesium oxide was significantly more effective.

EXAMPLE XIV

In the equipment described in Example I, the following materials were reacted at 28 inches vacuum:

| | |
|---|---|
| Polyethylene glycol (molecular weight 600) monomethyl ether | 480 grams |
| Urea | 50 grams |
| Magnesium oxide | 0.8 gram |

The heating sequence was as follows:

| Time | Temp. |
|---|---|
| 8:15 | 35° C. |
| 8:40 | 140° C. |
| 8:45 | 148° C. |
| 8:50 | 152° C. |
| 8:56 | 153° C. |
| 9:06 | 149° C. |
| 9:12 | 147° C. |
| 9:23 | 152° C. |
| 9:28 | 154° C. |
| 9:45 | 150° C. |
| 10:25 | 154° C. |
| 10:30 | 150° C. |

It will be understood that the foregoing examples have been provided to illustrate the invention. No limitation thereto is intended, since changes may be made in details of composition and method of operation without departing from the scope of the invention.

What is claimed is:

1. In a method for the manufacture of carbamates in which an alcohol is reacted with urea and ammonia is liberated, the improvement wherein the reaction is carried out at a temperature of at least 130° C., under a vacuum of at least 20 inches of mercury, said alcohol having a volatility no greater than that of diethylene glycol under the reaction conditions.

2. A method as set forth in claim 1 in which the vacuum is 28 inches.

3. A method as set forth in claim 1 in which the reaction is carried out in the presence of a catalyst selected from the group consisting of calcium, zinc and magnesium compounds.

4. A method as set forth in claim 3 in which the catalyst is selected from the group consisting of calcium oxide, zinc oxide and magnesium oxide.

5. A method as set forth in claim 1 in which the alcohol is diethylene glycol.

6. A method as set forth in claim 3 in which the alcohol is diethylene glycol.

7. In a method for the manufacture of carbamates in which an alcohol is reacted with urea under a vacuum, the improvement wherein the reaction is carried out in the presence of magnesium oxide as a catalyst.

8. A method as set forth in claim 7 in which a vacuum of at least 20 inches is applied.

9. A method as set forth in claim 8 in which a vacuum of 28 inches is applied.

10. A method as set forth in claim 8 in which the alcohol is diethylene glycol.

* * * * *